(12) United States Patent
Liang et al.

(10) Patent No.: US 11,440,930 B2
(45) Date of Patent: Sep. 13, 2022

(54) PREPARATION METHOD OF HIGH-PURITY TOTAL GINKGO FLAVONOL GLYCOSIDE AND APPLICATION OF SAME

(71) Applicant: SPH Xing Ling Sci. & Tech. Pharmaceutical Co., Ltd., Shanghai (CN)

(72) Inventors: Shuang Liang, Shanghai (CN); Xiangwei Zheng, Shanghai (CN); Qi Gao, Shanghai (CN); Dandan Wang, Shanghai (CN); Guoqin Zhu, Shanghai (CN)

(73) Assignee: SPH Xing Ling Sci. & Tech. Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/956,612

(22) PCT Filed: Apr. 10, 2018

(86) PCT No.: PCT/CN2018/082544
§ 371 (c)(1),
(2) Date: Nov. 6, 2020

(87) PCT Pub. No.: WO2019/119680
PCT Pub. Date: Jun. 27, 2019

(65) Prior Publication Data
US 2021/0054011 A1    Feb. 25, 2021

(30) Foreign Application Priority Data
Dec. 20, 2017    (CN) .......................... 201711383538.5

(51) Int. Cl.
*C07H 1/08* (2006.01)
*C07H 17/04* (2006.01)

(52) U.S. Cl.
CPC ............. *C07H 1/08* (2013.01); *C07H 17/04* (2013.01)

(58) Field of Classification Search
CPC .................................. C07H 1/08; C07H 17/04
See application file for complete search history.

(56) References Cited

FOREIGN PATENT DOCUMENTS

| CN | 101152222 A | * | 4/2008 | ............. A61K 36/16 |
|---|---|---|---|---|
| CN | 101152222 A | | 4/2008 | |
| CN | 101199560 A | * | 6/2008 | ............. A61K 36/16 |
| CN | 101596222 A | | 12/2009 | |
| CN | 101596222 B | * | 4/2012 | ............. A61K 36/16 |
| CN | 102727538 A | | 10/2012 | |
| CN | 102727538 B | * | 1/2015 | ............. A61K 36/16 |

OTHER PUBLICATIONS

Google Patents machine translation of CN 101596222 B, https://patents.google.com/patent/CN101596222B/en?oq=101596222, accessed online on Aug. 3, 2021. (Year: 2021).*
Google Machine translation of CN 101199560 A, https://patents.google.com/patent/, accessed online on Nov. 3, 2021. (Year: 2021).*
Li et al., Journal of Chromatography A, 2009, 1216, p8730-8740. (Year: 2009).*
Zhang CX et al., Bull. Environ. Contam. Toxicol. 2003, 71. p. 662-667. (Year: 2003).*
Google Machine translation of CN 101152222 A, https://patents.google.com/patent/, accessed online on Nov. 3, 2021. (Year: 2021).*
张济龙等 (Zhang, Jilong et al.)." 银杏叶黄酮提取溶剂研究 (Research of Solvents for Extracting Flavone from Ginkgo Leaves)" 西南农业大学学报 (Journal of Southwest Agricultural University),vol. 21, No. (02), Apr. 30, 1999(Apr. 30, 1999), pp. 181-182.

* cited by examiner

*Primary Examiner* — Jonathan S Lau

(57) ABSTRACT

The present disclosure relates to the field of pharmacology, and in particular, to a preparation method of high-purity total ginkgo flavonol glycoside. The preparation method of high-purity total ginkgo flavonol glycoside includes: (1) mixing *Ginkgo biloba* extract powder and a first alkaline solution, subjecting to dissolution and centrifugation to obtain a supernatant; (2) subjecting the supernatant to separation with an acid-polar coupled macroporous resin column and to purification with a polyamide column, to obtain high-purity total ginkgo flavonol glycoside. The purity of the total ginkgo flavonol glycoside prepared by the preparation method of high-purity total ginkgo flavonol glycoside according to the present disclosure is ≥90%, and has good clinical application prospects; the preparation process does not require organic reagents such as petroleum ether and ethyl acetate, which is environmentally friendly; the transfer rate of the total flavonol glycoside is high.

7 Claims, 2 Drawing Sheets

PREPARATION METHOD OF HIGH-PURITY TOTAL GINKGO FLAVONOL GLYCOSIDE AND APPLICATION OF SAME

CROSS REFERENCES TO RELATED APPLICATIONS

This is a Sect. 371 National Stage application of a PCT International Application No. PCT/CN2018/082544, filed on Apr. 10, 2018, which claims the benefits of priority of a Chinese Patent Application No. 2017113835385, entitled "Preparation Method of High-Purity Total Ginkgo Flavonol Glycoside and Application of Same", filed with CNIPA on Dec. 20, 2017, the contents of which are incorporated herein by reference in its entirety.

BACKGROUND OF THE PRESENT DISCLOSURE

Field of Disclosure

The present disclosure relates to the technical field of pharmacy, and in particular, to a preparation method of high-purity total ginkgo flavonol glycoside and application thereof.

Description of Related Arts

*Ginkgo biloba* extract powder (GBE50) is a kind of product with active ingredients extracted from the leaves of *Ginkgo biloba* L. by using appropriate solvents. Preparations made of GBE50 are widely used in medicine, health care products, food additives, functional beverages, cosmetics and other fields. Among them, in the field of medicine, *Ginkgo biloba* extract can be used for chest stuffiness and pains, stroke, hemiplegia, stiff tongue and sluggish speech caused by embolism stasis blocking channels; coronary heart disease stable angina pectoris, cerebral infarction, etc.

Ginkgo flavonoids are the active components of *Ginkgo biloba* extract, which have the effects of dilating blood vessels, inhibiting platelet activating factor, anti-oxidation and regulating blood lipid.

The purity of ginkgo flavonoids prepared by the conventional means is only about 44%, and the content of flavonol glycosides is only 24%, which limits the application and therapeutic effect of ginkgo flavonoids, especially the total ginkgo flavonol glycoside. Therefore, how to prepare high-purity ginkgo flavonol glycosides has always been a research focus in the field of pharmacy.

SUMMARY OF THE PRESENT DISCLOSURE

The present disclosure provides a total ginkgo flavonol glycoside and preparation method thereof, to prepare high-purity total ginkgo flavonol glycoside with purity equal to or greater than 90% (≥90%).

A first aspect of the present disclosure provides a method for preparing total ginkgo flavonol glycoside, including the following operations: (1) mixing *Ginkgo biloba* extract powder and a first alkaline solution, followed by dissolution and centrifugation to obtain a precipitation and a supernatant; (2) subjecting the supernatant to separation and purification by an acid-polar coupled macroporous resin column and a polyamide column, to obtain high-purity total ginkgo flavonol glycoside.

In one embodiment of the present disclosure, the dissolution in the operation (1) is an ultrasonic treatment, and the treatment time is 30~60 minutes.

In one embodiment of the present disclosure, the dissolution in the operation (1) is an ultrasonic treatment, and the treatment time is 30~45 minutes.

In one embodiment of the present disclosure, the dissolution in the operation (1) is an ultrasonic treatment, and the treatment time is 45~60 minutes.

In one embodiment of the present disclosure, the dissolution in the operation (1) is an ultrasonic treatment, and the treatment time is 30 minutes, 45 minutes or 60 minutes.

In one embodiment of the present disclosure, the first alkaline solution is a $Na_2CO_3$ aqueous solution with a mass fraction of 0.1~0.4%.

The mass fraction is expressed in a % which means a g solute per 100 ml of the solvent.

In one embodiment of the present disclosure, the first alkaline solution is a $Na_2CO_3$ aqueous solution with a mass fraction of 0.1~0.3%.

In one embodiment of the present disclosure, the first alkaline solution is a $Na_2CO_3$ aqueous solution with a mass fraction of 0.1~0.2%.

In one embodiment of the present disclosure, the first alkaline solution is a $Na_2CO_3$ aqueous solution with a mass fraction of 0.2~0.4%.

In one embodiment of the present disclosure, the first alkaline solution is a $Na_2CO_3$ aqueous solution with a mass fraction of 0.2~0.3%.

In one embodiment of the present disclosure, the first alkaline solution is a $Na_2CO_3$ aqueous solution with a mass fraction of 0.1%, 0.2%, 0.3% or 0.4%.

In one embodiment of the present disclosure, the operation (2) includes: loading the supernatant onto the acid-polar coupled macroporous resin column, and eluting with a second alkaline solution to obtain an eluent; drying the eluent to obtain a solid substance; dissolving the solid substance to obtain an acidic solution; loading the acidic solution onto the polyamide column, eluting with an aqueous ethanol solution, and drying to obtain the total ginkgo flavonol glycoside.

In one embodiment of the present disclosure, the diameter-height ratio of the acid-polar coupled macroporous resin column is 1:5~1:9.

In one embodiment of the present disclosure, the diameter-height ratio of the acid-polar coupled macroporous resin column is 1:5~1:7.

In one embodiment of the present disclosure, the diameter-height ratio of the acid-polar coupled macroporous resin column is 1:7~1:9.

As exemplified in some embodiments of the present disclosure, the diameter-height ratio of the acid-polar coupled macroporous resin column may be 1:5, 1:7 or 1:9.

In one embodiment of the present disclosure, the absorption ratio of the acid-polar coupled macroporous resin column is 1:30~1:50.

The absorption ratio refers to the mass ratio of the sample loaded to the resin used.

In one embodiment of the present disclosure, the absorption ratio of the acid-polar coupled macroporous resin column is 1:30~1:40.

In one embodiment of the present disclosure, the absorption ratio of the acid-polar coupled macroporous resin column is 1:40~1:50.

In one embodiment of the present disclosure, the absorption ratio of the acid-polar coupled macroporous resin column is 1:30, 1:40 or 1:50.

In one embodiment of the present disclosure, the second alkaline solution is a Na$_2$CO$_3$ aqueous solution with a mass fraction of 0.1~0.3%.

In one embodiment of the present disclosure, the second alkaline solution is a Na$_2$CO$_3$ aqueous solution with a mass fraction of 0.1~0.2%.

In one embodiment of the present disclosure, the second alkaline solution is a Na$_2$CO$_3$ aqueous solution with a mass fraction of 0.2~0.3%.

In one embodiment of the present disclosure, the second alkaline solution is a Na$_2$CO$_3$ aqueous solution with a mass fraction of 0.1%, 0.2%, or 0.3%.

In one embodiment of the present disclosure, the pH value of the acidic solution is 1~3.

In one embodiment of the present disclosure, the operation (1) includes mixing each 1 g of *Ginkgo biloba* extract powder with 20~50 ml of the first alkaline solution.

In one embodiment of the present disclosure, the operation (1) includes mixing every 1 g of *Ginkgo biloba* extract powder with every 20~30 ml of the first alkaline solution.

In one embodiment of the present disclosure, the operation (1) includes mixing every 1 g of *Ginkgo biloba* extract powder with every 20~25 ml of the first alkaline solution.

In one embodiment of the present disclosure, the operation (1) includes mixing every 1 g of *Ginkgo biloba* extract powder with every 25~50 ml of the first alkaline solution.

In one embodiment of the present disclosure, the operation (1) includes mixing every 1 g of *Ginkgo biloba* extract powder with every 25~30 ml of the first alkaline solution.

In one embodiment of the present disclosure, the operation (1) includes mixing every 1 g of *Ginkgo biloba* extract powder with every 30~50 ml of the first alkaline solution.

A second aspect of the present disclosure provides a total ginkgo flavonol glycoside prepared by the preparation method described in the first aspect.

Compared with the traditional technology, the present disclosure has the following beneficial effects:

The method for preparing total ginkgo flavonol glycoside according to the present disclosure can improve the purity of the total ginkgo flavonol glycoside, the purity of the prepared total ginkgo flavonol glycoside is equal to or greater than 90%, indicating good clinical application prospects. The preparation process is environmentally friendly as it does not require organic reagents such as petroleum ether and ethyl acetate. In addition, the transfer rate of the total flavonol glycoside is high.

DETAILED DESCRIPTION OF THE PREFERRED EMBODIMENTS

Before the embodiments according to the present disclosure are further described, it should be understood that the protection scope of the present disclosure is not limited to the specific embodiments described below. It should also be understood that the term in the examples according to the present disclosure is used to describe the particular implementation, and is not intended to limit the protection scope of the present disclosure. In the specification and claims according to the present disclosure, unless otherwise stated specifically, the singular forms "a", "an", and "the" comprise the plural forms.

When the numerical ranges are given by the examples, it should be understood that the two endpoints of each numerical range and any numerical value between the two endpoints can be selected, unless otherwise stated herein. Unless otherwise defined, all technical and scientific terms used in the present disclosure have the same meaning as commonly understood by those skilled in the art. In addition to the specific methods, devices and materials, any methods, devices, and materials of the prior art that are similar or equivalent to the methods, devices, and materials described in the examples according to the present disclosure can also be used to implement the present disclosure in accordance with the prior art known by those skilled in the art and the description of the present disclosure.

Embodiment 1

Operation 1. Separation of Total Ginkgo Flavonol Glycoside

Operation 11. Taking 5 g of *Ginkgo biloba* extract powder (GBE50) and slowly adding 100 ml of Na$_2$CO$_3$ aqueous solution with a mass fraction of 0.3% (pH value=9~10).

Operation 12. Dissolving by ultrasound for 60 minutes. Centrifuging at 10000 r/min, discarding the supernatant.

Figure 1:
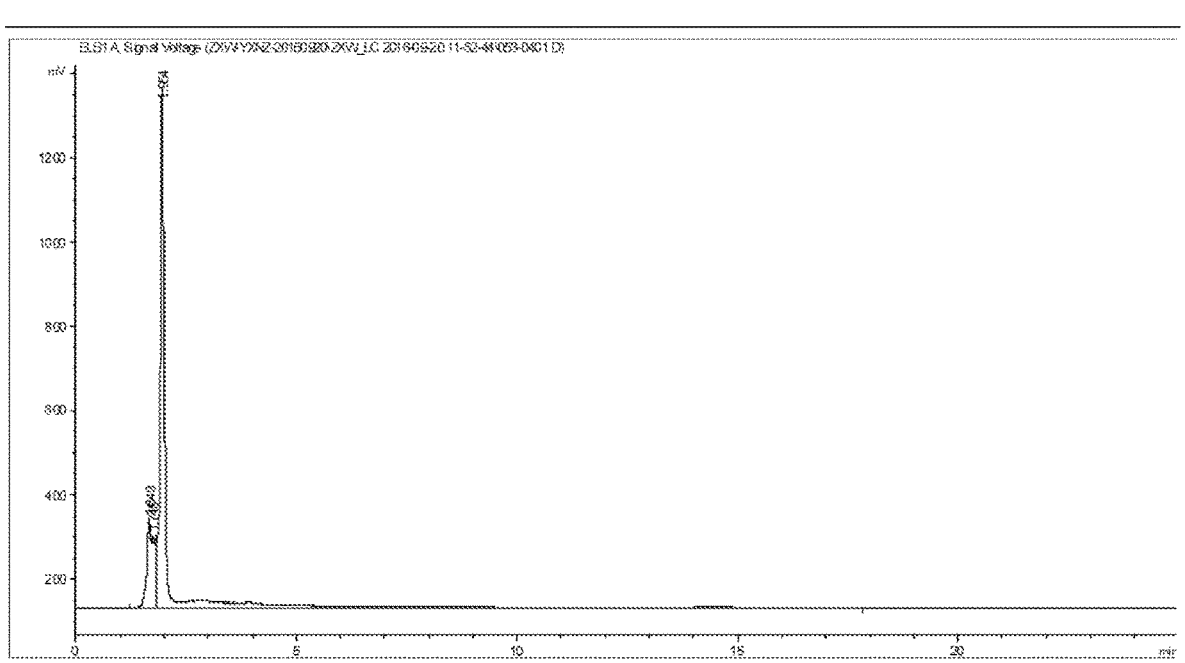
FIG. 1: Detection results of the supernatant obtained in operation 12 of the Embodiment 1 by using High Performance Liquid Chromatography-Evaporative Light Scattering Detector (HPLC-ELSD).

Using High Performance Liquid Chromatography-Evaporative Light Scattering Detector (HPLC-ELSD) to detect the supernatant obtained in operation 12. The results are shown in FIG. 1. Both peaks with Numbers represent solvent peaks, and there is no component peaks of ginkgolide. That is, no ginkgolide exists in the supernatant, which means the total ginkgo flavonol glycoside has been separated from *Ginkgo biloba* extract powder (GBE50) by alkaline-ultrasonic dissolution.

Operation 2. Enrichment of Total Ginkgo Flavonol Glycoside

Operation 21. Preparing an acid-polar coupled macroporous resin column. LSA-12S macroporous resin produced by Sunresin (Sunresin New Materials Co. Ltd, Xi'an, China) is selected as the acid-polar coupled macroporous resin. Pretreating the LSA-12S macroporous resin with acid and alkali. The diameter-height ratio of the LSA-12S macroporous resin column is 1:5, and the absorption ratio is 1:30. The absorption ratio refers to the mass ratio of the sample loaded to the resin used.

Operation 22. Loading the supernatant obtained in operation 12 onto the pretreated LSA-12S macroporous resin column in operation 21. Eluting with 5~6 column volumes of pure water, Na$_2$CO$_3$ aqueous solution with a mass fraction of 0.1%, pure water (eluting to neutral) and 95% aqueous ethanol in sequence. Collecting the eluent of Na$_2$CO$_3$ aqueous solution with a mass fraction of 0.1%, and concentrating by vacuum rotary evaporation at 55° C. to a powdery dry extract.

Figure 2A:
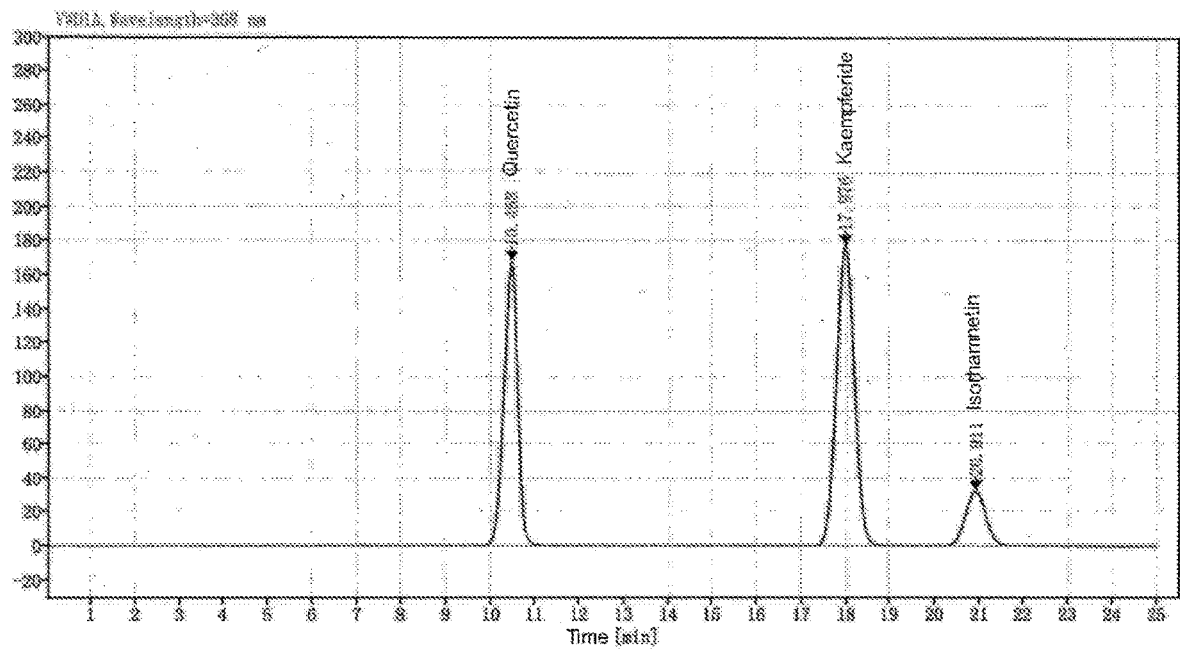
FIG. 2A: A mixed standard diagram of quercetin, kaempferide and isorhamnetin when using High Performance Liquid Chromatography-Ultraviolet (HPLC-UV) to detect the purity of the total ginkgo flavonol glycoside obtained in operation 23 of Embodiment 1.
Figure 2B:
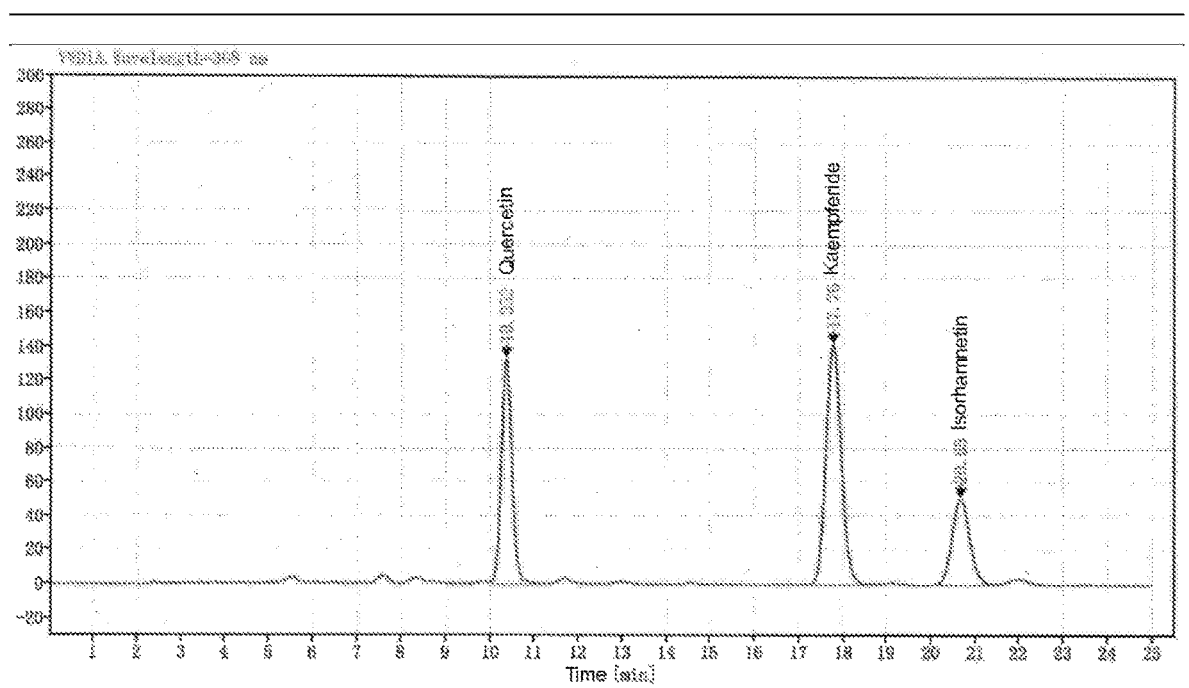
FIG. 2B: HPLC-UV diagram of the sample when using High Performance Liquid Chromatography-Ultraviolet (HPLC-UV) to detect the purity (≥90%) of the total ginkgo flavonol glycoside obtained in operation 23 of Embodiment 1.

Operation 23. Dissolving the powdery dry extract obtained in operation 22 by ultrasound with 40 ml dilute hydrochloric acid, and adjusting the pH value to 2 with dilute hydrochloric acid. Loading the sample onto the polyamide column chromatography; eluting with 5 column volumes of pure water and 20%, 80%, 95% aqueous ethanol in sequence, collecting the 80% aqueous ethanol eluent; concentrating to dryness by rotary evaporation at 55° C.; weighing 0.42 g, the mixture containing high-purity total ginkgo flavonol glycoside is obtained. As shown in FIGS. 2A and 2B, according to the measurement result of HPLC-UV, the mass of the total ginkgo flavonol glycoside in the mixture containing high-purity total ginkgo flavonol glycoside is 0.39 g. Therefore, it can be known that the purity of the total ginkgo flavonol glycoside obtained in operation 23 is 92%. The transfer rate of total ginkgo flavonol glycoside is greater than 50%.

The transfer rate is the mass ratio of the total ginkgo flavonol glycoside in the mixture containing high-purity total ginkgo flavonol glycoside prepared in operation 23 to the total ginkgo flavonol glycoside contained in 5 g GBE50 powder in operation 11.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 2

In this Embodiment, the absorption ratio in operation 21 is replaced with 1:40, and the other operations are the same as those in Embodiment 1. The purity of the obtained total ginkgo flavonol glycoside is 91%, and the transfer rate of the total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 3

In this Embodiment, the absorption ratio in operation 21 is replaced with 1:50, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 4

In this Embodiment, the pH value in operation 23 is adjusted to 1 with dilute hydrochloric acid, and the other operations are the same as those in Embodiment 1. The purity of the obtained total ginkgo flavonol glycoside is 92%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 5

In this Embodiment, the pH value in operation 23 is adjusted to 3 with dilute hydrochloric acid, and the other operations are the same as those in Embodiment 1. The purity of the obtained total ginkgo flavonol glycoside is 94%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high; the preparation process does not require organic reagents such as petroleum ether and ethyl acetate, which is environmentally friendly; the transfer rate of the total flavonol glycoside is high.

Embodiment 6

In this Embodiment, the ultrasonic dissolution time in operation 12 is 45 minutes, and the other operations are the same as those in Embodiment 1. The purity of the obtained total ginkgo flavonol glycoside is 92%. The transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 7

In this Embodiment, the ultrasonic dissolution time in operation 12 is 30 minutes, and the other operations are the same as those in Embodiment 1. The purity of the obtained total ginkgo flavonol glycoside is 90%. The transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 8

In this Embodiment, the operation 11 includes taking 1 g of GBE50 powder and adding 30 ml of $Na_2CO_3$ aqueous solution with a mass fraction of 0.3%, and the other operations are the same as those in Embodiment 1. The purity of the obtained total ginkgo flavonol glycoside is 91%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 9

In this Embodiment, the operation 11 includes taking 10 g of GBE50 powder and adding 250 ml of $Na_2CO_3$ aqueous solution with a mass fraction of 0.3%, and the other operations are the same as those in Embodiment 1. The purity of the obtained total ginkgo flavonol glycoside is 90%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 10

In this Embodiment, the operation 11 includes taking 2 g of GBE50 powder and adding 100 ml of $Na_2CO_3$ aqueous solution with a mass fraction of 0.3%, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 11

In this Embodiment, the operation 11 includes taking 7 g of GBE50 powder and adding 300 ml of $Na_2CO_3$ aqueous solution with a mass fraction of 0.3%, and the other operations are the same as those in Embodiment 1. The purity of the obtained total ginkgo flavonol glycoside is 92%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 12

In this Embodiment, the operation 11 includes taking 1 g of GBE50 powder and adding 50 ml of $Na_2CO_3$ aqueous solution with a mass fraction of 0.3%, and the other operations are the same as those in Embodiment 1. The purity of the obtained total ginkgo flavonol glycoside is 90%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 13

In this Embodiment, the operation 11 includes taking 10 g of GBE50 powder and adding 200 ml of $Na_2CO_3$ aqueous solution with a mass fraction of 0.3%, and the other operations are the same as those in Embodiment 1. The purity of the obtained total ginkgo flavonol glycoside is 91%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 14

In this Embodiment, the $Na_2CO_3$ aqueous solution with a mass fraction of 0.3% in the operation 11 is replaced with $Na_2CO_3$ aqueous solution with a mass fraction of 0.2%, and the other operations are the same as those in Embodiment 1. The purity of the obtained total ginkgo flavonol glycoside is 92%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 15

In this Embodiment, the $Na_2CO_3$ aqueous solution with a mass fraction of 0.3% in the operation 11 is replaced with $Na_2CO_3$ aqueous solution with a mass fraction of 0.1%, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 16

In this Embodiment, the $Na_2CO_3$ aqueous solution with a mass fraction of 0.3% in the operation 11 is replaced with $Na_2CO_3$ aqueous solution with a mass fraction of 0.4%, and the other operations are the same as those in Embodiment 1. The purity of the obtained total ginkgo flavonol glycoside is 91%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 17

In this Embodiment, the operation 11 includes taking 1000 g of GBE50 powder and adding 20000 ml of $Na_2CO_3$ aqueous solution with a mass fraction of 0.3%, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 18

In this Embodiment, the diameter-height ratio of the LSA-12S macroporous resin column in the operation 21 is 1:7, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 19

In this Embodiment, the diameter-height ratio of the LSA-12S macroporous resin column in the operation 21 is 1:9, and the other operations are the same as those in Embodiment 1. The purity of the obtained total ginkgo flavonol glycoside is 93%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

Embodiment 21

In this Embodiment, the $Na_2CO_3$ aqueous solution during the eluting process in operation 22 has a mass fraction of 0.3%, and the other operations are the same as those in Embodiment 1. The purity of the obtained total ginkgo flavonol glycoside is 91%; the transfer rate of total ginkgo flavonol glycoside is greater than 50%.

The purity of the total ginkgo flavonol glycoside prepared by the present Embodiment is ≥90%, and has good clinical application prospects; the preparation process does not require organic reagents such as petroleum ether and ethyl acetate, which is environmentally friendly; the transfer rate of the total flavonol glycoside is high.

To sum up, compared with the traditional technology, the present disclosure has the following distinguishing features:

1) *Ginkgo biloba* extract powder (GBE50) is directly used as the raw material instead of *Ginkgo biloba* leaves or general ginkgo extract; 2) ginkgo flavonoids and ginkgolide are separated from the raw materials by the method of alkaline-ultrasonic dissolution, and no patents related to this separation method have been reported; 3) The macroporous resin material is the modified macroporous resin LSA-12S, and this is the first time that this material is applied to the enrichment of active components of ginkgo. 4) Unlike the two-stage alkaline solution elution in the traditional technology, the present disclosure adopts a single-stage alkaline solution elution method.

Further, compared with the traditional technology, the present disclosure has the following beneficial effects:

1) the purity of the ginkgo flavonol glycoside of the present disclosure is greater than 90%, which is not lower than the effect of traditional technology; 2) the final transfer rate of the ginkgo flavonol glycoside of the present disclosure reaches 51.8%, which is ideal; 3) the present disclosure has a pilot-scale test of 1000 g raw material, the result shows good repeatability and good industrialization prospect; 4) the present disclosure does not involve low-boiling, toxic and harmful organic reagents such as petroleum ether and ethyl acetate, which is environmentally friendly.

In summary, the present disclosure effectively overcomes various shortcomings and has high industrial utilization value.

The above-mentioned embodiments are just used for exemplarily describing the principle and effects of the present disclosure instead of limiting the present disclosure. Those skilled in the art can make modifications or changes to the above-mentioned embodiments without going against the spirit and the range of the present disclosure. Therefore, all equivalent modifications or changes made by those skilled in the art without departing from the spirit and scope of the disclosure will be covered by the appended claims.

The invention claimed is:

1. A method for preparing a total ginkgo flavonol glycoside, comprising the following operations:
   (1) mixing *Ginkgo biloba* extract powder with a first alkaline solution, subjecting to dissolution and centrifugation to obtain a supernatant;
   (2) subjecting the supernatant to separation and purification by an acid-polar coupled macroporous resin column and a polyamide column, to obtain a high-purity total ginkgo flavonol glycoside; wherein
   a diameter-height ratio of the acid-polar coupled macroporous resin column is 1:5~1:9; and
   an absorbtion ratio of the acid-polar coupled macroporous resin column is 1:30~1:50.

2. The preparation method according to claim 1, wherein the dissolution in operation (1) is an ultrasonic treatment, and an ultrasonic time is 30~60 minutes.

3. The preparation method according to claim 1, wherein the first alkaline solution is a $Na_2CO_3$ aqueous solution with a mass fraction of 0.1~0.4%.

4. The preparation method according to claim 1, wherein operation (2) comprises: loading the supernatant onto the acid-polar coupled macroporous resin column, and eluting with a second alkaline solution to obtain an eluent; drying the eluent to obtain a solid substance; dissolving the solid substance to obtain an acidic solution; loading the acidic solution onto the polyamide column, eluting with an aqueous ethanol solution, and drying to obtain the total ginkgo flavonol glycoside.

5. The preparation method according to claim 4, wherein the second alkaline solution is a $Na_2CO_3$ aqueous solution with a mass fraction of 0.1~0.3%.

6. The preparation method according to claim 4, wherein a pH value of the acidic solution is 1~3.

7. The preparation method according to claim 1, wherein operation (1) comprises mixing every 1 g of *Ginkgo biloba* extract powder with every 20~50 ml of the first alkaline solution.

* * * * *